United States Patent [19]

Boyd et al.

[11] Patent Number: 5,134,120

[45] Date of Patent: Jul. 28, 1992

[54] USE OF GROWTH HORMONE TO ENHANCE PORCINE WEIGHT GAIN

[75] Inventors: R. Dean Boyd; Dale E. Bauman, both of Ithaca; Walter R. Butler, Freeville, all of N.Y.

[73] Assignee: Cornell Research Foundation, Inc., Ithaca, N.Y.

[21] Appl. No.: 333,878

[22] Filed: Apr. 4, 1989

Related U.S. Application Data

[63] Continuation of Ser. No. 925,474, Oct. 31, 1986, abandoned, which is a continuation of Ser. No. 637,642, Aug. 3, 1984, abandoned.

[51] Int. Cl.⁵ .............................................. A61K 37/02
[52] U.S. Cl. ........................................ 514/12; 514/21
[58] Field of Search ..................... 424/108; 514/12, 21

[56] References Cited

U.S. PATENT DOCUMENTS

| | | | |
|---|---|---|---|
| 3,239,418 | 3/1966 | Perlman | 424/108 |
| 4,423,072 | 12/1983 | Stahly | 514/552 |
| 4,521,409 | 6/1985 | Bauman et al. | 514/2 |
| 4,610,976 | 9/1986 | Bohlen et al. | 514/12 |

OTHER PUBLICATIONS

Machlin, J. Animal Sci. 35, 794–800, 1972.
Chung et al., J. Animal Sci. 57, 190, 1983.
Peel et al., J. Nutrition, 1111 (9), 1662–1671, 1981.
Anderson et al., J. Endocrin. 68:345–346, 1976.
J. Dairy Sci., 65:1375–1389 (1982).
Reicherts, Methods in Enzymology, 37:360–380 (1975).
Wilhelmi et al., J. Biol. Science 176:735–745 (1948).
McCutcheon et al., J. Dairy Sci., 67:2881–2886 (1984).
Boyd et al., 1985, Cornell Nutrition Conference Proceedings, pp. 10–19.
Spence et al., J. Animal Sci. 60:1280–1287 (1985).
Stahly et al., J. Animal Sci., 50(Suppl 1):222.
Kveragas et al., 1985 Proceedings Georgia Nutrition Conference Proceedings, pp. 102–107.
Boyd, Proc. 1979 Cornell Nutrition Conference, pp. 102–107.
Hartsock et al., J. Animal Sci., 44:320–330 (1977).
Seeburg et al., DNA, 2:37–45 (1983).
Forsyth, Biochemistry of Lactation, Mepham, ed. Elsevier Sci. Pub. 1983, Chpt. 10, pp. 309–349.
Chung et al., J. Animal Sci. 60:118–130 (1985).
Boyd et al., J. Animal Sci., 47:883–892 (1978).
Wassmuth et al., Tierzuchtg Zuchtapbiol. 90:56–64 (1973) (and translation thereof).
Boyd et al., Proc. 1983 Cornell Nutrition Conference, pp. 108–113.
Spence et al., Abstract of presentation at Am. Soc. Animal Sci., Aug. 7–10, 1984 meeting. "Effect of Exogenous Growth Hormone on Fetal Energy Storage . . .".
Spence et al., Abstract of presentation at Am. Soc. Animal Sci. Aug. 7–10, 1984 meeting. "Effect of Exogenous Porcine Growth Hormone on Metabotic and Endocrine Patterns in Sows During Late Gestation and Lactation".
Bell et al., J. Biol. Chem., 260:8520–8525 (1985).
Bines et al., J. Dairy Sci., 1982, 65:1375–1389.
Mellenberger et al., Biochem. J., 136:741–748 (1973).
Collier et al., Endocrinology, 100:1192–1200 (1977).
Akers et al., Endocrinology, 109:23–40 (1981).
Sejrsen, Acta Agric. Scandinavica, 1978, 28:41–45.
Sejrsen et al., Livestock Prod. Sci., 1977, 4:313–325.
Sejrsen et al., J. Dairy Sci., 1982 65:793–800.
Tucker, J. Dairy Sci., 1981, 64:1403–1421.

*Primary Examiner*—Jacqueline Stone

[57] ABSTRACT

This invention relates to deliberately increasing growth hormone in swine during the last 2 weeks of pregnancy through a 3 week lactation. This has the effect of increasing fetal energy storage during late pregnancy which resulted in the newborn piglets having marked enhancement of the ability to maintain plasma concentrations of glucose and free fatty acids when fasted after birth. Likewise, treatment of the sow during lactation results in increased milkfat in the colostrum and an increased milk yield. These effects are important in enhancing survivability of newborn pigs and weight gain prior to weaning.

4 Claims, 4 Drawing Sheets

USE OF GROWTH HORMONE TO ENHANCE PORCINE WEIGHT GAIN

This application is a continuation of application Ser. No. 925,474, filed Oct. 31, 1986, which is a continuation of application Ser. No. 637,642, filed Aug. 3,1984 both now abandoned.

BACKGROUND OF THE INVENTION

The effect of growth hormone on pregnant or lactating sows has not been previously investigated. Nutritional treatments which increase fetal energy storage and/or elevate colostral fat percent have been demonstrated to improve the survival rate of "newborn" pigs Stahly et al., J. Anim. Sci., 1980, 51:222 (Supplement 1); Boyd et al., J. Anim. Sci., 1978, 47:883. Likewise, elevated milk production increases weaning weights of the piglets but present methods to accomplish this encompass only genetic selection. To date, published literature contains few studies with metabolic hormones on fetal energy storage or lactation effects in swine; but no reports exist for growth hormone.

Peel et al. J. Nutr., 1981, 111:1662, describes the administration of bovine growth hormone to high yielding cows and demonstrated that at peak milk production, milk yield was enhanced by growth hormone. Milk production returned to normal levels following cessation of the treatment.

Machlin et al., J. Anim., 1972, 35:794, Wassmuth, R. and H. Renter, Z. Tiersuchtg Zuchtgsbiol., 1973, 90:56 and Chung et al., J. Anim. Sci., 1983, 57:190 (Supplement 1) demonstrated that daily administration of growth hormone to older growing pigs improved daily gain and efficiency of feed utilization. The former demonstrated decreased fat content of the carcass.

DESCRIPTION OF THE INVENTION

Figure 1:
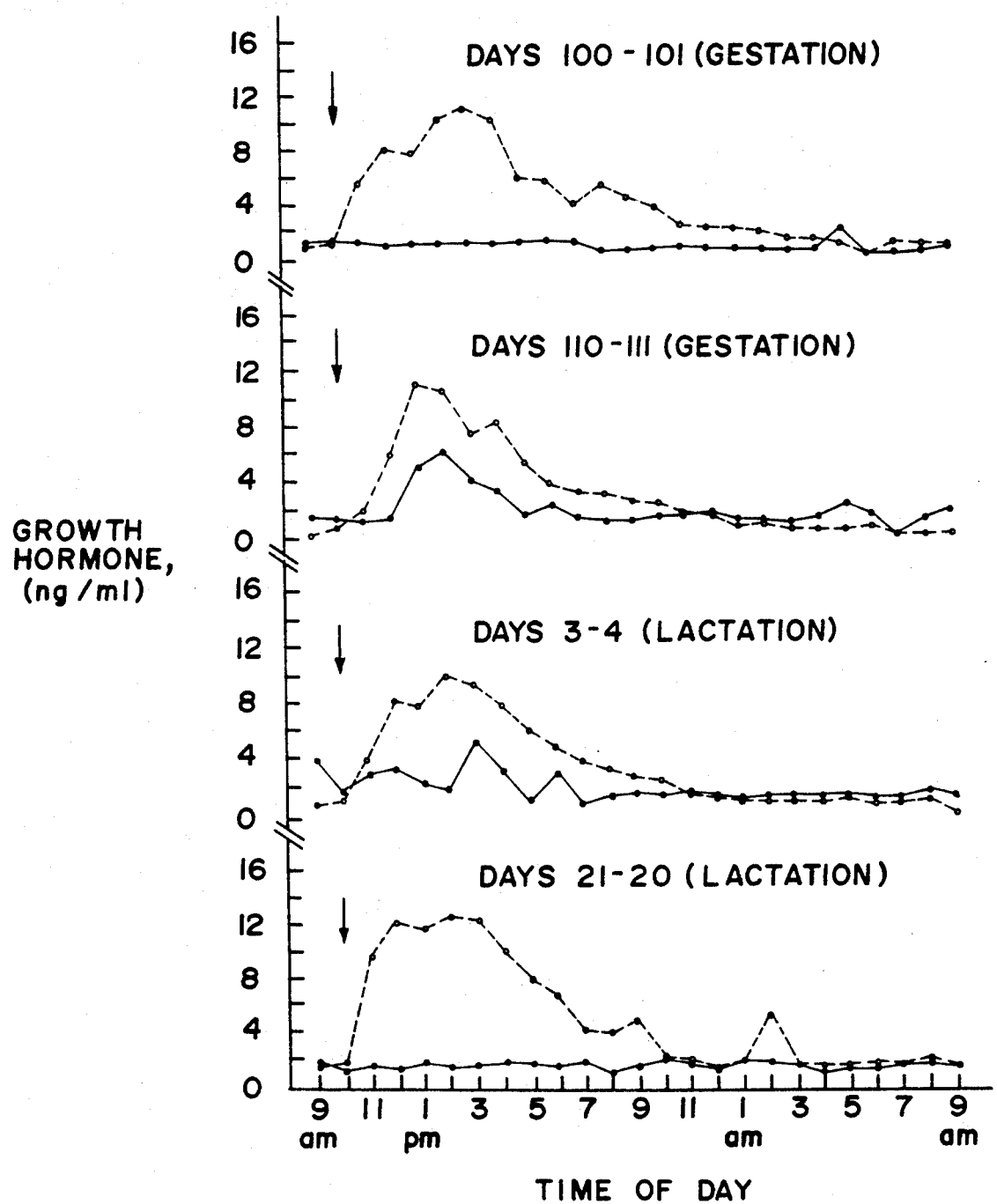
FIG. 1 shows the plasma growth hormone profile of sows during the injection period. Each point is the mean of 3 sows. Blood plasma samples were taken every hour and arrows indicate the time of injection of growth hormone ●—● or placebo ○—○.

This invention relates to deliberately increasing growth hormone in swine during the last 2 weeks of pregnancy through a 3 week lactation. The deliberate increasing of growth hormone in a swine can be accomplished by two modes employing direct or indirect exogenous means, i.e. by the administration of exogenous growth hormone or by the administration of exogenous factors which enhance secretion of growth hormone from the pituitary gland, an amount sufficient and for a time sufficient to cause the swine to internally generate blood levels of growth hormone equivalent to those achieved by the direct administration of exogenous growth hormone. This has the effect of increasing fetal energy storage during late pregnancy which resulted in the newborn piglets having marked enhancement of the ability to maintain plasma concentrations of glucose and free fatty acids when fasted after birth.

In another embodiment of the invention, treatment of the sow during lactation results in increased milkfat in the colostrum and an increased milk yield.

These effects are important in enhancing survivability of newborn pigs and weight gain prior to weaning.

The exogenous growth hormone employed in this invention can be naturally occurring growth hormone isolated from animal tissues or a body fluid (for example porcine growth hormone isolated from pituitary glands), or it can be a synthetic equivalent of a naturally occurring growth hormone (for example a growth hormone produced by recombinant DNA techniques).

The deliberate growth hormone increase (the treatment to increase circulating concentrations of growth hormone) in the pregnant/ post parturient female porcine is an amount sufficient, for a time sufficient to provide newborn with increased fetal energy and to enhance milkfat in the mothers colostrum and milk yield. Typically, the amount of exogenous growth hormone administered is in the range of about 0.2 to about 20.0 milligrams per 100 kilograms of porcine body weight, daily. An effective amount can be monitored by increased serum growth hormone levels as compared to the animal when the exogenous hormone is withdrawn. Alternatively circulating concentrations of growth hormone can be enhanced by the administration of compounds which increase the pituitary secretion of this hormone since the secretion rate is controlled by a balance between inhibitory factors (such as somatostatin) and stimulatory factors (such as GRF (growth hormone releasing factor)). The exogenous growth hormone or compound to stimulate growth hormone secretion can be administered in any manner adopted to cause entry into the blood stream. For example, while subcutaneous injection is presently preferred, the growth hormone can also be given intramuscularly or intravenously. The use of time release implants is also contemplated.

The period of time during which increased growth hormone is caused for the purposes stated herein appears to be reasonably critical. For fetal energy enhancing purposes of the invention, the growth hormone level should be increased during the last trimester of pregnancy but the beneficial effects of this invention involving growth hormone level increase appears to be greatest in the last 2 weeks of pregnancy when fetal energy storage is most rapid. A shorter increased growth hormone interval is anticipated if the lactation component is desired independent of pregnancy effects. The practical period to effect milk production would be to commence treatment just prior to or soon after parturition and last substantially until nursing neonates are weaned.

EXAMPLES

Effect of Exogenous Porcine Growth Hormone On Fetal Energy Storage And Lactation Performance Sixteen sows and gilts were used in this study in which an isolated porcine growth hormone (GH) preparation (USDA-pGH-B-1, 2.1 IU/mg) was administered during the latter part of gestation through a 21-day lactation. Daily injections (1000h) of either placebo (excipient) or GH (8.9IU) were given subcutaneously beginning on day 100 of gestation. Three of 8 sows/treatment were cannulated and blood samples acquired hourly (24 to 30 h period) on days 99 (pre-injection), 100 and 110 of gestation and days 3 and 21 of lactation. Plasma GH levels in placebo-treated animals remained relatively constant (approximately 1.5–2.0 ng/ml) throughout the treatment period. Limited episodic response was observed on day 3 of lactation. For the GH treatment group, plasma GH peaked (7 to 10 times greater than basal concentration) 3–5 hours after GH injection and declined to baseline levels 8–12 hours later. Mean daily elevation of plasma GH (area under the curve to baseline) in GH females was higher ($P<.10$) throughout the study. Treatment with GH effected a 2–2.5 fold increase ($P<.10$) in plasma free fatty acids (FFA) except for day 21 where treatment response was similar. Plasma glucose and insulin response was similar between treatment groups. Parturition was induced on day 113 ($PGF_{2\alpha}$). Two pigs/litter were sacrificed at birth and 2 were fasted for 24h. Pigs from GH-treated sows had 292 mg of glycogen/ 100g body weight which was 6.6% greater than the placebo group (274). Plasma glucose was higher in pigs from GH sows than pigs from placebo sows after 12h (76 vs 62 mg/100ml) and 24h (70 vs 57 mg/100ml) of fasting. Plasma FFA concentration after the 24h fast was 162 $\mu Eq/l$ (GH) and 127 (placebo). These differences represent increases of 23% in glucose and 29% in FFA. Milk samples were collected at parturition and on days 13 and 20 of lactation. Percent fat was 26% greater in colostrum from GH sows (not significant). Percent protein was decreased ($P<.01$) in colostrum (14.93 vs 17.47) for GH sows but similar on day 13 (4.82 vs 5.06) and day 20 (4.81 vs 5.19 for GH and placebo, respectively. GH and placebo-treated sows had similar milk yields at 2 weeks (6.96 vs 6.76 kg/day, respectively) but yield was 16% greater by 3 weeks for GH sows (6.89 vs 5.94). This coincided with a 26% reduction ($P<.01$) in lactation feed intake and greater backfat loss ($P<.10$) during the experiment for GH sows.

Materials and Methods

Sixteen crossbred (Yorkshire × Duroc) first and second parity sows were used in this study. All sows were fed approximately 2.27 kg daily of a corn-soybean meal diet (14% protein) fortified with vitamins and minerals at 0600h during gestation and were fed ad libitum during lactation. On day 91 of gestation chronic catheters were placed in the vena cava of three sows per treatment according to the procedure of Ford and Maurier (1978). Sows initially received 1g of thiopental sodium (pentothal sodium, Abbott, North Chicago, Ill.), given intravenously and anesthesia was maintained by halothane (fluothane, Ayerst, New York, N.Y.) inhalation. The catheter passed subcutaneously to the shoulder of the animal where it was exteriorized. The exposed catheter end was protected underneath a canvas patch containing a zippered opening to facilitate blood sample collection. The six catheterized animals allowed investigation of the metabolic and hormonal response of the sow in addition to the effects on the newborn and lactation. The five sows per treatment which remained uncatheterized were used solely for examination of treatment effects on the newborn pigs an lactational performance.

Sow backfat and body weight were recorded on day 97 of gestation. Beginning on day 100 of gestation, sows were randomly allotted within parity to one of two treatment groups and injected subcutaneously with either placebo or 8.9 IU (7.4 IU for first-parity sows) of porcine growth hormone (GH). Injections were administered daily at 1000h continuing through a 21 day lactation period. Activity of the isolated GH preparation (USDA-pGH-B-1) was determined to be 2.1 IU/mg using a rat tibia test. The dosage of 8.9 IU·sow$^{-1}$·day$^{-1}$ was based on work in growing pigs (Machlin, 1972) and a preliminary study we performed in which the plasma GH peak was 5 to 7 times higher than the basal level. The growth hormone for injection was solubilized in a saline solution containing 0.05M $NaHCO_3 + Na_2CO_3$ to produce an injection volume of 5ml. Control animals received a placebo injection of 5ml of the buffered saline.

Blood samples were obtained from the catheterized sows at 1300h on alternate days throughout the 35 day period. Based on research in cattle, it was estimated that the daily peak of plasma growth hormone would occur at 1300h. In addition, sows were intensively sampled at 1h intervals on days 99 through 101 (54h period) and 110 through 111 (24h period) of gestation and days 3 through 4 (24h period) and 21 through 22 (30h) of lactation. Blood samples (5ml) were drawn from the exposed catheter end into syringes. The blood for growth hormone and insulin analysis (3ml) was placed in a glass tube containing sodium heparin, and that for glucose and free fatty acid (FFA) analysis (2ml) was placed in a glass tube containing sodium fluoride and potassium oxalate. Tubes were gently rolled and placed immediately on ice until centrifugation. Following centrifugation, plasma fractions were transferred to plastic tubes and frozen ($-10C$) until analyzed. Plasma glucose and FFA were determined only for fractions at 3h intervals for intensive sampling periods. Plasma glucose was measured by automated analysis (technicon 2 autoanalyzer, Technicon Instruments Corp., Tarrytown, N.Y.) using a modification of the glucose oxidase method (Gochman and Schmitz, 1972). Plasma FFA concentration was determined using an automated procedure based on the colorimetric method of Dalton and Kowalski (1967). Radioimmunoassay with iodinated insulin was used to measure plasma concentration of insulin (Herbert et al., 1965) and growth hormone (Marple and Aberle, 1972). The modified method for determination of porcine growth hormone was prepared in our laboratory. Standards used in both assays were: porcine insulin (lot #615-073-256) and porcine growth hormone USDA-pGH-B-1).

Parturition was synchronously induced by intramuscular injection of 10mg of prostaglandin $F_{2\alpha}$ at 0800h on day 113 of gestation with sows farrowing on day 114. Two pigs per litter were subjected to a 24h fast initiated at birth and two additional pigs per litter were sacrificed for liver glycogen determination. Each litter was standardized and maintained at 9 pigs/litter for first parity sows and 10 pigs/litter for second parity sows throughout the 21 day lactation period. Pigs to undergo fasting were obtained during farrowing and a blood sample was collected from each immediately after birth. These pigs were removed from the sow, weighed and placed in an environmentally controlled room (32±1C) in individual cages with water available ad libitum. Blood samples (approximately 3ml) were obtained from pigs via the anterior vena cava with a 22-gauge needle at 0, 12 and 24h after birth. Blood was collected into an evacuated glass tube containing sodium heparin and immediately chilled on ice until centrifugation. Following centrifugation, the plasma fraction was removed to a plastic tube and frozen (−10C) until analyzed. Plasma glucose and FFA were determined as stated previously.

Pigs designated for liver glycogen determination were removed immediately after birth, weighed, mechanically stunned, and killed by exsanguination. As rapidly as possible the liver was removed, blotted free of blood and weighed (without gall bladder). A corresponding lobe was excised from the liver of each pig and frozen in liquid nitrogen. The liver portions were stored at −10C until analyzed. Liver glycogen concentration was determined by the colorimetric method (Lo et al., 1970). Three subsamples per selected lobe were each analyzed for two aliquot volumes in duplicate to achieve a mean glycogen concentration for each liver.

Sow back fat, body weight, litter weight and milk production and composition was determined to analyze the effect of growth hormone administration on lactation performance. Sow backfat was measured ultrasonically on days 97 and 113 of gestation and day 22 of lactation. Sow body weight was recorded on day 97 of gestation and day 22 of lactation. Litter weights were recorded at birth and on day 21 of lactation. Milk samples were expressed manually at the time of farrowing (colostrum) and on day 13 and day 20 of lactation. An intramuscular injection of 40 IU of oxytocin was administered (except for colostrum collection) and two glands per sow were milked as rapidly as possible until no more milk was given. The samples from the two glands were mixed thoroughly and aliquots deposited in two vials and preserved with potassium dichromate. Vials were frozen (−10C) until analysis. Milk fat, dry matter and protein was determined according to A.O.A.C. (1980) procedures, and milk lactose was analyzed by a semi-automated (model 27 industrial analyzer, Yellow Springs Instrument Co., Inc., Yellow Springs, Ohio) enzymatic procedure (operating procedure no. OP-025, Monsanto Co., St. Louis, Mo.). The milk yield of each sow was determined on days 13 and 20 by weighing the pigs at hourly intervals before and after nursing as described by Lewis et al. (1978) and Mahan et al. (1971). Each nursing and weighing period lasted approximately 10 min. and care was taken to prevent or account for urine and fecal losses during this time. The initial two nursing periods were used to acclimate the sow and litter and were not included in computation of the daily milk yield. Milk yield was calculated by multiplying by four the yield obtained during the subsequent 6 hours.

Area under the response curve was calculated for sow plasma metabolite and hormone response for a 24 hour interval (900h to 900h) during each intensive sampling period. Area was expressed as area above the axis or area above the baseline (which corrects for differences in basal concentration between animals). Data were analyzed by an appropriate application of analysis of variance procedures for the one-way classification (area under curve, production), randomized block design (liver glycogen) or split-plot (fasting glucose, FFA and lactation response). These were computed using the Statistical Analysis System (SAS Institute 1982). The sow was defined as the experimental unit. The "t" test was utilized to compare treatment means within time for fasting data and milk composition. Orthogonal contrasts were calculated to define the time response where appropriate. Steel and Torrie (1960) was used as a reference for statistical procedures.

Results and Discussion

Previous studies involving growth hormone administration to swine have reported toxicity problems (Doyle et al., 1956; Machlin, personal communication) which range from loss of appetite to muscular convulsions and death in some animals. In this study, the dosage of growth hormone was one-fifth that employed by Doyle et al. (1956) but adverse effects were still observed. Three sows experienced difficult breathing which was attributed to GH administration since placebo sows failed to show similar effects. Approximately 5–7 days after initiation of the injections, two sows exhibited labored and shallow breathing. One of them went off feed and was removed from the study, whereas, another recovered the following day without any apparent problems thereafter. The third sow exhibited similar symptoms on day 112 of gestation but recovered.

The effect of GH administration to sows on plasma glucose, FFA, GH and insulin is summarized in table 1. Area under the response curve is presented in table 2.

TABLE 1

SUMMARY OF CONCENTRATIONS OF PLASMA METABOLITES AND HORMONES IN SOWS BEFORE, DURING AND AFTER TREATMENT PERIOD[a]

| Variable | | | | |
|---|---|---|---|---|
| Glucose, mg/100 ml | Pre-injection, | 99 | 85 | 90 |
| | injection, | 100 | 87 | 93 |
| | | 110 | 83 | 95 |
| | | 3 | 90 | 104 |
| | | 21 | 87 | 97 |
| | Post-injection, | 22 | 85 | 90 |
| FFA, μEq/L | Pre-injection, | 99 | 142 | 76 |
| | injection, | 100 | 99 | 227 |
| | | 110 | 135 | 297 |
| | | 3 | 127 | 279 |
| | | 21 | 122 | 107 |
| | Post-injection, | 22 | 119 | 74 |
| Growth hormone, ng/ml | Pre-injection, | 99 | 1.38 | 1.98 |
| | injection, | 100 | 1.44 | 7.26 |
| | | 110 | 3.54 | 5.76 |
| | | 3 | 2.56 | 6.02 |
| | | 21 | 1.54 | 8.21 |
| | Post-injection, | 22 | 1.54 | 1.71 |
| Insulin, ng/ml | Pre-injection, | 99 | 1.16 | 1.45 |
| | injection, | 100 | 1.24 | 1.18 |
| | | 110 | 0.49 | 1.55 |
| | | 3 | 2.58 | 5.28 |
| | | 21 | 1.68 | 2.55 |
| | Post-injection, | 22 | 1.85 | 3.04 |

[a] Means represent data for 3 sows/treatment. Glucose and FFA were analyzed at 3 h intervals. Growth hormone and insulin were analyzed hourly. Pre-injection period represents 24 h from 0900 h on day 99 to 0800 h on day 100. Injection periods represent 12 h from 1100 h to 2200 h for GH and insulin, 1200 h to 2400 h for glucose and FFA. Post-injection period represents 12 h from 0400 h to 1500 h. The times given encompass the period of GH elevation due to daily injection.

TABLE 2

METABOLITE AND HORMONE RESPONSE OF SOWS TO GROWTH HORMONE INJECTIONS: AREA UNDER THE CURVE

| Day | glucose[a] placebo | GH | FFA[b] placebo | GH | Growth hormone[c] placebo | GH | Insulin[c] placebo | GH |
|---|---|---|---|---|---|---|---|---|
| | | | Area above axis | | | | | |
| 99 | 588.3 | 623.3 | 1006.0 | 546.7 | 32.2 | 33.0 | — | — |
| 100[d] | 606.3 | 645.3 | 827.3 | 1610.0+ | 32.6 | 113.9* | — | — |
| 110[d] | 574.0 | 669.0* | 1066.7 | 1941.3* | 53.9 | 83.2 | — | — |
| 3 | 684.7 | 709.3 | 965.7 | 1690.0 | 46.5 | 84.9 | 68.8 | 100.6 |
| 21[d] | 616.7 | 664.0 | 932.0 | 707.3 | 37.3 | 120.9* | — | — |
| | | | Area above baseline | | | | | |
| 99 | 51.7 | 30.7 | 562.7 | 173.3 | 3.6 | 1.0 | — | — |
| 100[d] | 76.7 | 52.7 | 325.7 | 1190.0+ | 2.9 | 79.8* | — | — |
| 110[d] | 72.3 | 36.7 | 588.3 | 1381.3+ | 19.2 | 66.0+ | — | — |
| 3[d] | 122.3 | 60.7 | 347.3 | 908.3 | 8.0 | 64.2+ | 37.4 | 52.7 |
| 21[d] | 77.7 | 66.7 | 313.7 | 299.0 | 3.9 | 91.4** | — | — |

[a]Units are mg · min/dl.
[b]Units are μEq · min/L.
[c]Units are ng · min/ml.
[d]GH means with superscripts are different from placebo means in the same row and column heading;
**$P < .01$,
*$P < .05$,
+$P < .10$.

Plasma GH was elevated a maximum of 7 to 10 times the basal level (FIG. 1). Peak concentration (10.0 to 12.6 ng/ml) occurred 3 to 5 hours after the GH injection and declined to basal levels (1.5 to 2.0 ng/ml) approximately 10h later. In sows receiving a placebo injection, the concentration of plasma GH remained relatively constant (averaging 1.5 to 2.0 ng/ml) except for day 110 of gestation and day 3 of lactation when episodic elevation occurred (reaching 6.4 ng/ml at one point). On day 110, the elevation observed was predominantly due to high values for one sow. Her pattern of plasma GH suggested that GH injection preparation may have been mistakenly flushed into her cannula in place of the citrate maintenance solution. The plasma GH of this sow peaked very high and dropped quickly: her plasma GH data was adjusted for the 4 hour peak period to correspond to her previous values. The episodic pattern of GH elevation observed in placebo sows on day 3 appears to be natural. Area above the GH baseline (table 2) is significantly greater ($P<.01$ to $P<.01$) throughout the treatment period for GH sows compared with placebo sows. No significant differences were observed in area above the axis for plasma GH on days 110 and 3 due to the episodic elevation observed in the placebo group.

Figure 4:
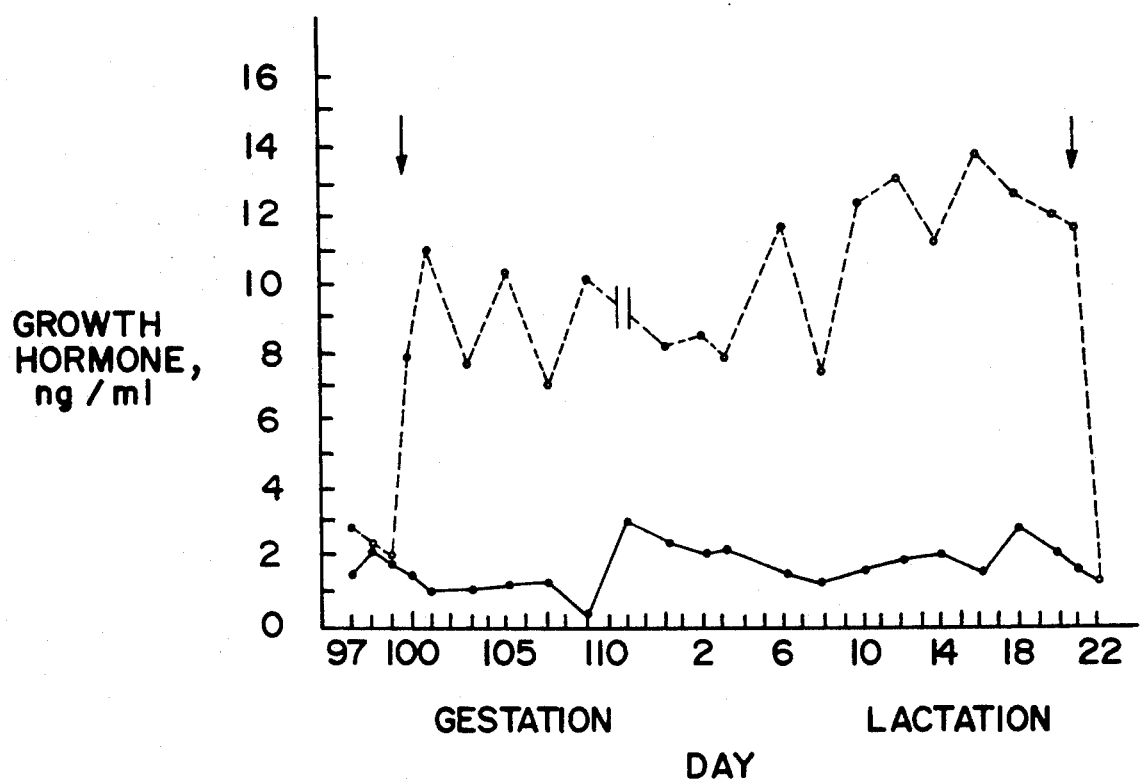
FIG. 4 shows the mean daily plasma growth hormone concentration of sows during the experimental period. Each point is the mean of 3 sows. Blood plasma samples were taken at 1300 hours. Arrows denote first (day 100) and last (day 21) growth hormone ●—● or placebo ○—○ injections (1000 hours daily).

The daily GH profile presented in FIG. 4 indicates plasma GH was elevated to a similar extent (mean, 9 ng/ml) until days 10 through 21 when the mean elevation was 12.5 ng/ml. A similar observation has been reported in cattle (Peel et al., 1983).

Figure 2:
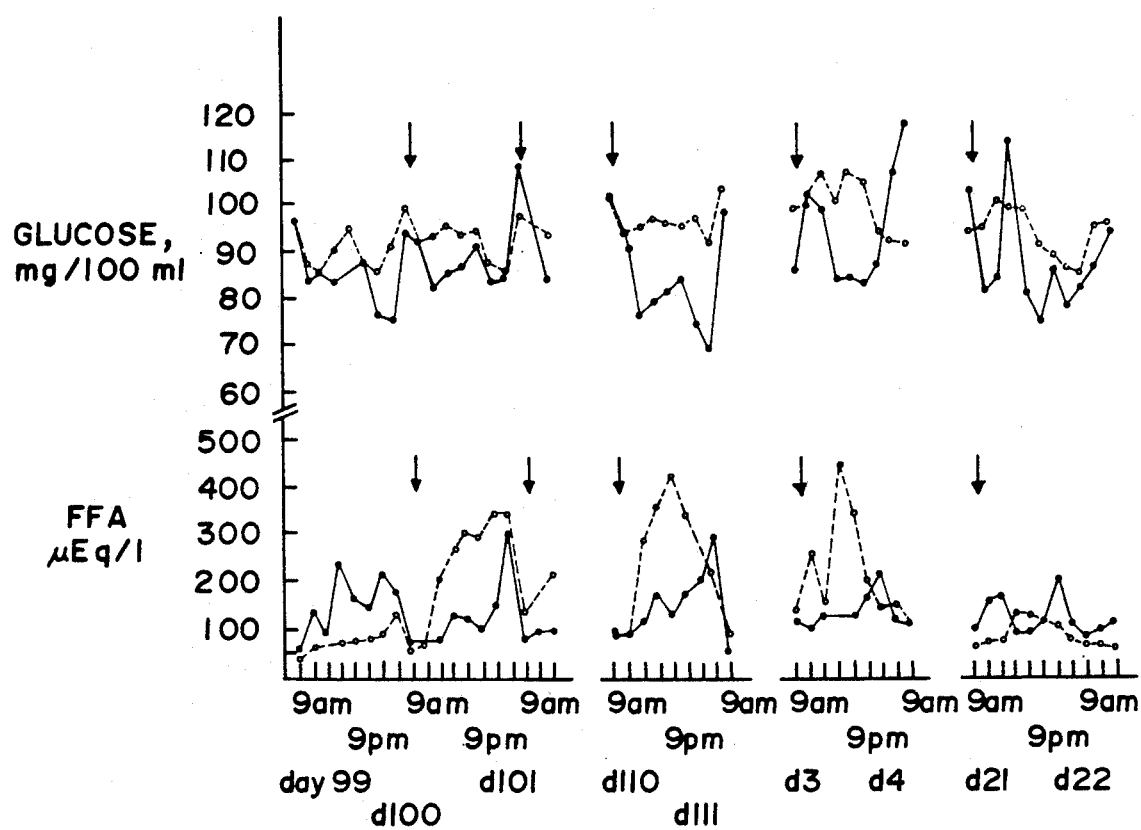
FIG. 2 shows the plasma glucose and free fatty acid profiles of sows during the injection period. Each point is the mean of 3 sows. Blood plasma samples were taken every 3 hours. Arrows indicate time of injection of growth hormone ●—● or placebo ○—○.

Injection of the GH isolate resulted in a two-fold increase in the plasma FFA concentration at each sampling period except day 21 (table 1, FIG. 2). The increase is even more pronounced when area above the baseline is considered. This may be particularly important since GH sows appeared to be markedly different on day 99 or pre-injection (area above axis, $P<.10$).

There was a delay of approximately 2 to 5 hours between GH injection and FFA elevation but plasma concentration remained high for 12 to 18 hours. Free fatty acid concentration reached maximum approximately 8 to 10 hours post-injection, suggesting a true lipolytic response as opposed to the rapid rise in FFA observed due to impurities in early preparations of GH (Peel, 1982). The absence of the lipolytic effect in late lactation may be due to depletion of mobilizable lipid stores and/or a change in receptor concentration or affinity. The dramatic difference in weight loss and backfat observed in GH sows support the former possibility.

Elevation of plasma FFA appeared to coincide with a slight increase in plasma glucose toward the end of gestation (day 110, FIG. 2 and tables 1 and 2). This difference ($P<.05$) was not apparent the first day of injection (day 100). Increased availability of FFA for oxidation by maternal tissues may account for the increase in glucose. Likewise, GH may have reduced the effectiveness of an insulin mediated decline in plasma glucose post-feeding. Potentially, the net effect would be greater glucose availability to the fetus for tissue development and energy storage.

Figure 3:
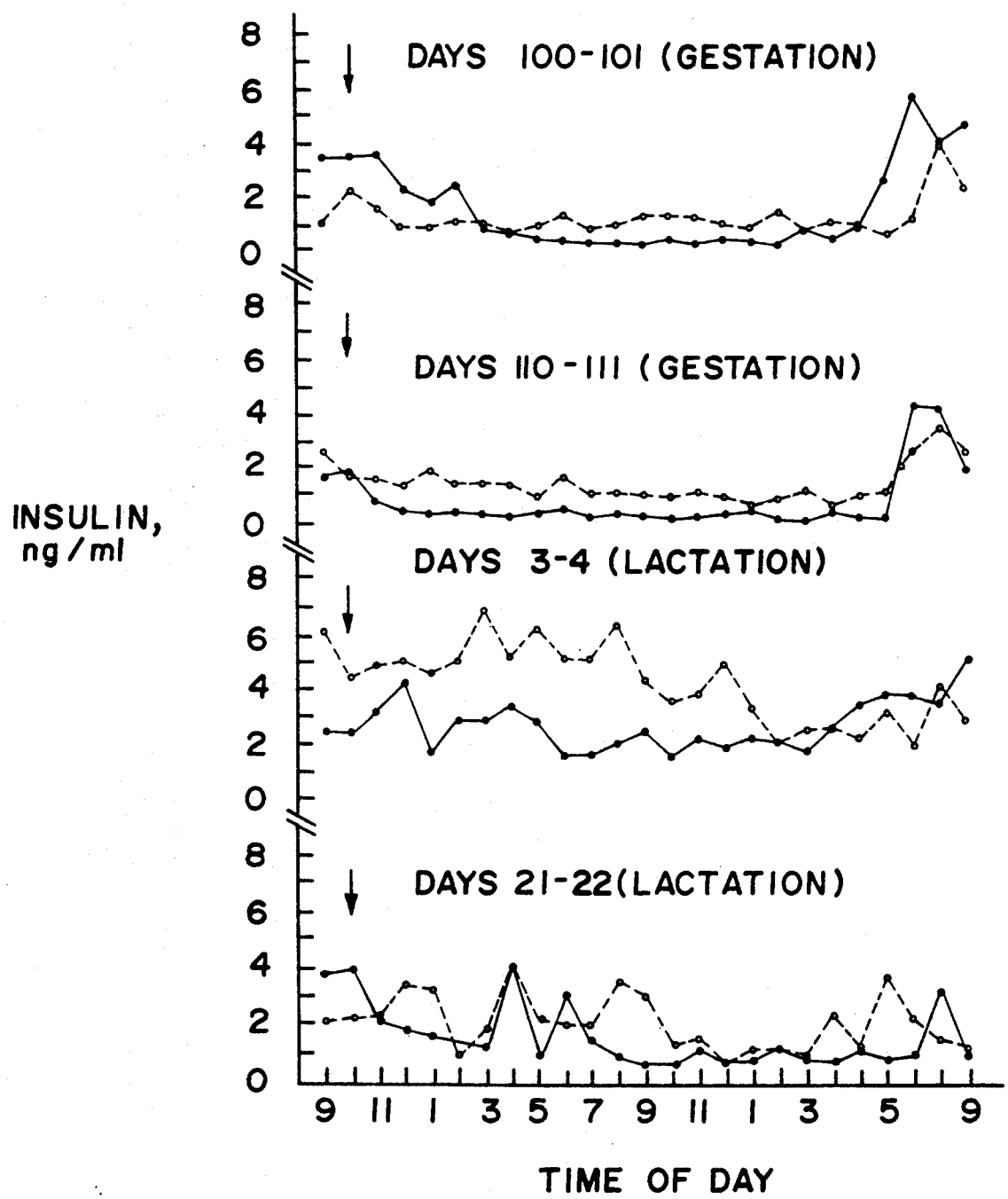
FIG. 3 shows the plasma insulin profile of sows during the injection period. Each point is the mean of 3 sows. Blood plasma samples were taken every hour and arrows indicate the time of injection of growth hormone ●—● or placebo ○—○.

Plasma insulin response was similar between treatment groups (FIG. 3, table 1). Area under the curve was computed for day 3 of lactation since this was the only day in which a potential difference appeared to exist. Neither area above the axis or baseline were significant ($P>.10$). Insulin pattern became more episodic on day 3, most likely due to the change from once-a-day to ad libitum feeding which was initiated at parturition.

The effect of maternal GH administration on liver glycogen content in progeny at birth is presented in table 3. Total glycogen and glycogen per unit of body weight was greater in pigs from GH sows (3.88g, 292 mg/100 g) compared to the placebo group (3.52 g, 274 mg/100 g). This represents a 6.6% increase which is marginal and not statistically different ($P>.10$).

TABLE 3

EFFECT OF GROWTH HORMONE ADMINISTRATION TO SOWS ON LIVER GLYCOGEN CONTENT IN PIGS AT BIRTH

| Item | Treatment of sows Placebo | GH | Pooled CV, % |
|---|---|---|---|
| No. litters - pigs | 8–16 | 8–16 | |
| Birth wt., g | 1244 | 1346 | |
| Liver wt., g | 33.7 | 40.5 | |
| Glycogen, mg/g | 90.8 | 89.6 | |
| Total glycogen, g | 3.52 | 3.88 | |
| Glycogen: body wt., mg/100 g | 274 | 292 | |

TABLE 4

EFFECT OF GROWTH HORMONE ADMINISTRATION TO SOWS ON PLASMA FFA AND GLUCOSE OF PIGS FASTED FROM BIRTH

| Item | time, h | placebo | GH | CV, % |
|---|---|---|---|---|
| No. litters - pigs | | 8–16 | 8–15 | |
| Birth wt., g | | 1347 | 1358 | |
| Glucose, mg/100 ml[a] | 0 | 48 | 57 | |
| | 12 | 62 | 76 | |
| | 24 | 57 | 70 | 21.7 |
| FFA, µEq/L[b] | 0 | 81 | 83 | |
| | 12 | 148 | 128 | |
| | 24 | 127 | 162 | 45.1 |

[a]Time linear (P < .01) and quadratic (P < .01).
[b]Time linear (P < .01) and quadratic (P < .05).

The metabolic response to fasting by newborn pigs is presented in table 4. Plasma glucose concentration at birth and throughout the 24 hour fast was higher for pigs derived from GH sows. Maximum levels were observed after 12 hours of fasting in both treatment groups (76 vs 62 mg/100ml for GH and placebo, respectively), which declined to 70 and 57 mg/100ml after 24 hours. Although not statistically significant, this represents a 23% difference in plasma glucose concentration between GH and placebo groups. Plasma FFA concentrations were similar at birth and averaged 82 µEq/L (table 4). Lower values after 12 hours for pigs from GH sows (128 µEq/L) compared with placebo pigs (148) may be due to higher plasma glucose in the GH group, however no treatment × time effect was observed. FFA levels after 24 hours were 28% higher in pigs from GH sows (162 µEq/L compared to placebo (127). Both groups exhibited a quadratic (P<.05) FFA and glucose pattern, suggesting mobilization of lipid and glycogen stores followed by failure to maintain lipolysis and glycogenolysis.

Exogenous growth hormone administration has been shown to consistently increase milk yield and milk fat yield in dairy cattle (Machlin, 1973; Bines et al., 1980; Peel et al., 1983). The summary of lactation performance (table 5) for this study shows a similar milk yield for both GH (6.96 kg/day) and placebo (6.76) sows at 2 weeks of lactation (day 13). By day 20, milk yield of GH sows (6.89 kg/day) was 16% higher than that of placebo sows (5.95) although differences were not significant. Administration of GH appeared to buffer against a decline in milk production since the 20-day yield was similar to 12-day performance (6.89 vs 6.96 kg/day). In contrast, there was a 12% decrease by the control group (5.94 vs 6.76 kg/day; treatment × time, P<.11). This ability to maintain milk production with advancing lactation is important especially between 14–28 days since pigs are rapidly outgrowing maternal ability to satisfy nutrient needs.

TABLE 5

EFFECT OF GROWTH HORMONE ADMINISTRATION TO SOWS TO LACTATIONAL PERFORMANCE[a]

| | colostrum | | Day 13 | | Day 20 | | |
|---|---|---|---|---|---|---|---|
| Variable | placebo | GH | placebo | GH | placebo | GH | CV, % |
| Mammary secretion, kg/d | | | | | | | |
| Milk[b] | — | — | 6.76 | 6.96 | 5.94 | 6.89 | 9.4 |
| Fat | — | — | .46 | .54 | .42 | .45 | |
| Protein | — | — | .34 | .34 | .31 | .33 | |
| Lactose | — | — | .31 | .31 | .30 | .36 | |
| Milk composition, % | | | | | | | |
| Fat | 6.11 | 7.67 | 6.87 | 7.71 | 6.99 | 6.51 | 22.6 |
| Protein[c,d] | 17.47[1] | 14.93[2] | 5.06 | 4.82 | 5.19 | 4.81 | 11.8 |
| Lactose[e] | 2.84 | 2.70 | 4.65 | 4.52 | 4.97 | 5.18 | 12.9 |

[a]Means represent data for 8 sows/treatment.
[b]Time. P < .10; treatment × time effect, P < .11.
[c]Treatment, P < .01; Treatment × time, P < .01.
[d]Means in the same row with different superscripts are different P < .11.
[e]Time linear and quadratic, P < .01.

TABLE 6

SOW PERFORMANCE AND LITTER DATA[a]

| | Treatment | | |
|---|---|---|---|
| Item | placebo | GH | CV, % |
| Sow feed intake, kg/d[b] | 4.68 | 3.48** | 15.3 |
| Sow wt. change, kg[c] | +2.1 | −9.6* | 249.1 |
| Sow backfat change, cm[c] | −.06 | −.35+ | 131.9 |
| Birth wt. of pigs, g[d] | 1330 | 1370 | 13.8 |
| Weaning wt. of pigs, g[d] | 4450 | 4520 | 23.0 |
| Weight gain of pigs, g[d] | 3120 | 3150 | 31.7 |

[a]Means represent data for 8 sows/treatment.
[b]Means for the 21-day lactation period only.
[c]Means for the entire 35-day treatment period.
[d]Means are for the 9 (first parity sows) or 10 (second parity sows) pigs in the standardized litter for a 21-day lactation.
*P < .05
**P < .01
+P < .10

The 16% increase in milk yield of GH sows coincided with a 26% decrease (P<.01) in feed intake (table 6). Enhanced mobilization from adipose tissue reserves apparently contributed to the sow's ability to increase milk yield despite a substantial reduction in feed intake. Sows receiving GH lost more backfat (−0.35 cm, P<.10) and weight (table 6; −9.6 kg, P<.0.05) during the experimental period when compared to the placebo group (−0.06 cm, +2.1 kg). Reduction of feed intake by 3 to 16% has been reported in short term studies with dairy cattle (Machlin, 1973; Bines et al., 1980; Peel et al., 1981; Peel et al., 1983, Fronk et al., 1983).

Enhancement of energy density (fat %) in sow colostrum and milk could result in improved survivability of the smaller, less-competitive newborn pig (Boyd et al., 1978a). Fat percentage of colostrum was increased 26% in GH sows (7.67 vs 6.11%, not significant). On day 13, a 12% increase in fat percentage resulted in a 17% increase in fat yield. By day 20, no differences in fat yield or percentage were evident. This coincides with a diminished lipolytic response as indicated previously (FIG. 2).

Virtually no difference was observed between treatment groups in birth (1.33 vs 1.37 kg/pig) or weaning weight (4.45 vs 4.52 kg/pig) for placebo or GH progeny respectively.

Percent protein was decreased (P<.01) in colostrum of GH sows (14.93%) compared with that of the placebo group (17.47%). This depression in protein concentration did not persist throughout lactation. Protein yield was virtually identical between groups on days 13 and 20. Lactose percentage and yield were similar for GH and placebo-treated sows at all sampling times. Lactose concentration was low in colostrum (2.84 and 2.70%, placebo and GH respectively) and increased through day 13 to reach approximately 5.0% on day 20.

Results of this study provide evidence that GH can improve the energetic status of pigs at birth and milk production. Ability to achieve the former may depend on its capability to mobilize fatty acids. The fasting data indicate that newborn pigs which are unable to effectively compete with littermates would be in a much better position metabolically. The glucose levels maintained during fasting in GH pigs were equivalent to the advantage achieved in the nutritional approaches undertaken. The latter approach has been demonstrated effective in enhancing survival by 0.3-0.6 pigs/litter.

We claim:

1. A method of enhancing the weight gain of newborn pigs which comprises increasing growth hormone levels in the mother during lactation by the subcutaneous, intramuscular, or intravenous administration of exogenous means selected from porcine growth hormone or growth hormone releasing factor in an amount sufficient and for a time sufficient to increase growth hormone levels in the mother to maintain milk production with advancing lactation and thereby to enhance weight gain in the newborn pigs prior to weaning.

2. The method of claim 1 where said exogenous means is exogenous porcine growth hormone.

3. The method of claim 2 where the porcine growth hormone is administered in an amount between about 0.2 to about 20.0 milligrams of growth hormone per 100 kilograms of porcine body weight, daily.

4. The method of claim 1 wherein the growth hormone is administered subcutaneously.

* * * * *